US00PP11288P

United States Patent [19]

Fear et al.

[11] Patent Number: Plant 11,288

[45] Date of Patent: Mar. 14, 2000

[54] PEACH TREE NAMED 'SUPECHNINE'

[75] Inventors: Carlos D. Fear, Aptos; Bruce D. Mowrey, La Selva Beach; David W. Cain, Bakersfield, all of Calif.

[73] Assignee: Sun World International Inc., Bakersfield, Calif.

[21] Appl. No.: 09/007,512

[22] Filed: Jan. 15, 1998

[51] Int. Cl.[7] ..... A01H 5/00

[52] U.S. Cl. ..... Plt./197

[58] Field of Search ..... Plt./197

[56] References Cited

U.S. PATENT DOCUMENTS

| | | | |
|---|---|---|---|
| P.P. 966 | 7/1950 | Vetter | Plt./197 |
| P.P. 4,903 | 10/1982 | Weinberger | Plt./198 |
| P.P. 5,388 | 1/1985 | Goosen | Plt./197 |
| P.P. 5,503 | 7/1985 | Weinberger | Plt./198 |

*Primary Examiner*—Howard J. Locker
*Assistant Examiner*—Wendy A Baker
*Attorney, Agent, or Firm*—Knobbe, Martens Olson & Bear, LLP

[57] ABSTRACT

A new and distinct variety of peach tree characterized by its early ripening fruit which has a round shape, lacking a protruding tip, and an almost uniform red coloration.

1 Drawing Sheet

BACKGROUND AND SUMMARY OF THE INVENTION

This invention relates to the discovery and asexual propagation of a new variety of hybrid peach tree, *Prunus persica* cv. Supechnine. The tree produces a medium-sized and round-shaped fruit that has a red over color that is more uniform and less striped than that of similar or related varieties. The new peach tree variety arose from a controlled cross made by Carlos D. Fear, was first selected and evaluated by Bruce D. Mowrey and David W. Cain, and was asexually propagated by Bruce D. Mowrey. Its pollen parent is Supechthree (U.S. Plant Pat. No. 4,903) and its seed parent is Supechfour (U.S. Plant Pat. No. 5,503).

The new peach tree variety cv. Supechnine may be distinguished from other presently available peach cultivars, particularly the Maycrest cultivar (U.S. Plant Pat. No. 4,064), by the following combination of characteristics: its larger size, a more uniform and less striped red over color, a more desirable round shape (Supechnine lacks the undesirable protruding tip of the Maycrest variety), a firmer flesh, and ripening that occurs 12 days after the Maycrest variety. The new variety holds these distinguishing characteristics through succeeding asexual propagations by budding, in the vicinity of Wasco, Kern County, Calif.

Among the characteristics which distinguish the new variety of peach tree from its pollen parent, Supechthree, are the following: the new variety ripens approximately 7 days later than Supechthree, it has a more desirable round shape, a more uniform and less striped red over color, and a larger size. Further, Supechnine has fewer undesirable doubled fruits and fewer split pits than its pollen parent.

The new variety may be distinguished from its seed parent, Supechfour, by the following characteristics: it ripens approximately 7–10 days earlier than the seed parent, the fruit size of the new variety is slightly smaller, and in years with cool wet weather during bloom, the new variety has a lower fruit set and produces a greater number of undesirable undeveloped fruits than Supechfour.

The new variety may be distinguished from the Ray Crest variety (U.S. Plant Pat. No. 5,388) by having different parentage, by having a more desirable uniform red blush as opposed to the more striped red blush of Ray Crest, and by having a more desirable rounded apex as opposed to the protruding apex of Ray Crest. The suture of the new variety is smoother and less protruding than that of the Ray Crest variety and the fruits are more nearly round in shape. Fruits of the new variety lack the conspicuous yellow suture line of Ray Crest, Maycrest, and other Springcrest (unpatented) mutations.

The new variety can be distinguished from the unnamed peach tree variety that is described in U.S. Plant Pat. No. 966 by blooming earlier than U.S. Plant Pat. No. 966 more nearly with or before July Elberta (unpatented), the parent of U.S. Plant Pat. No. 966. The new variety ripens approximately 20 days before U.S. Plant Pat. No. 966. The new variety has showy (sh/sh) light pink flowers as opposed to nonshowy (Sh/-) salmon colored flowers of U.S. Plant Pat. No. 966. The new variety has a more nearly round fruit shape and lacks the mammiform apex of U.S. Plant Pat. No. 966.

DETAILED BOTANICAL DESCRIPTION OF THE INVENTION

Figure 1:
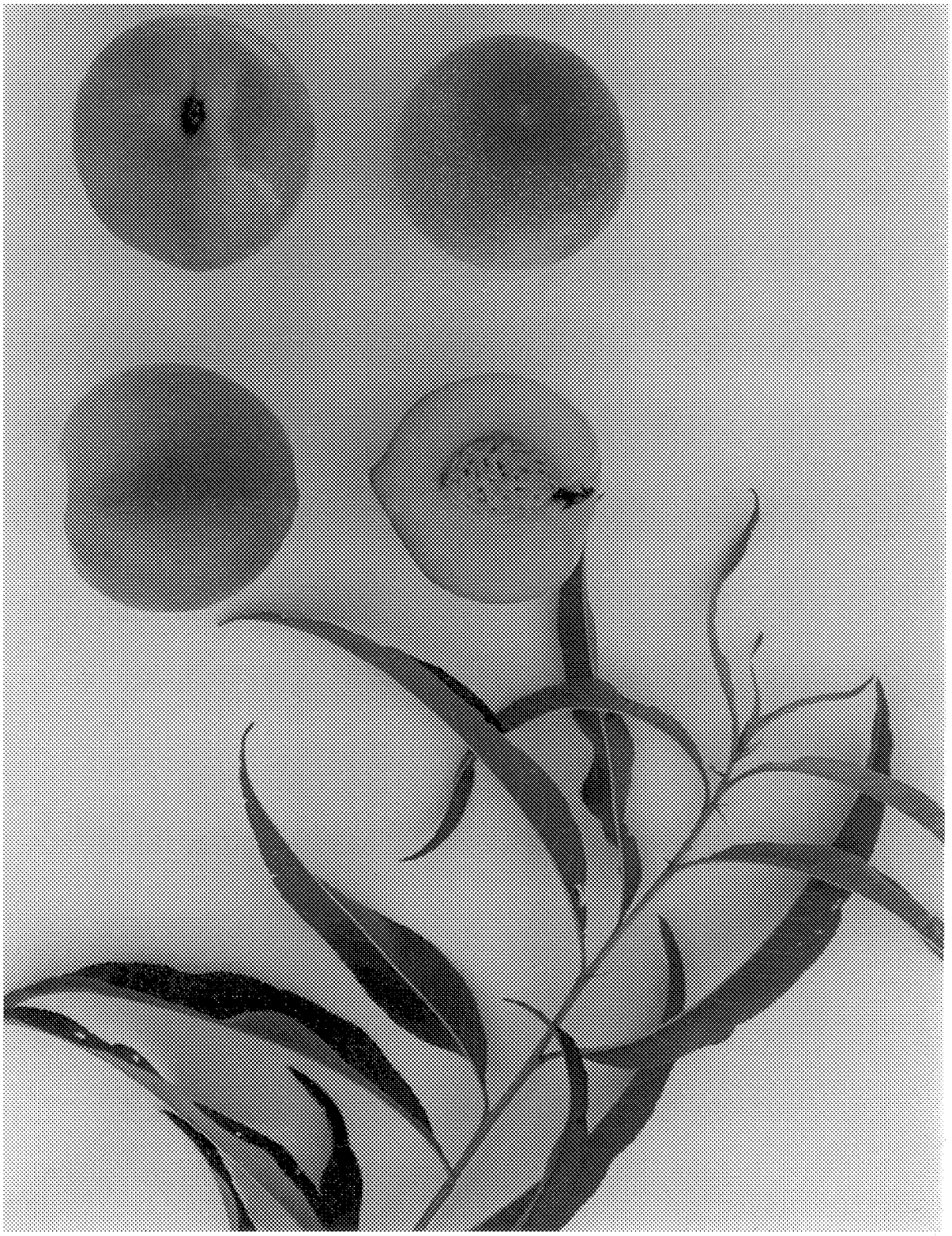
FIG. 1 illustrates, in full color, a typical stem and mature leaves of the peach tree and the ripe fruit as viewed from the stem and in profile. The drawing also illustrates the fruit sectioned in half from end to end, one-half of the fruit shown with the stone in place in the flesh. The colors illustrated are as accurate as reasonably possible to attain in color photographic reproductions of this type.

Throughout this specification, color names beginning with a small letter signify that the name of that color, as used in common speech, is aptly descriptive. Color names with capital letters designate values based upon the R.H.S. Colour Chart, published by The Royal Horticultural Society, London. The botanical description herein follows the UPOV test guideslines for peach varieties.

The descriptive matter which follows pertains to peach trees of the new variety grafted onto Nemared root stock and grown in the vicinity of Wasco, Kern County, Calif. during 1993 and is believed to apply to plants grown under similar conditions of soil and climate elsewhere. Such trees were three years old, and were maintained at a height of about 10 feet and a crown diameter of about 10 feet by annual prunings.

When grafted on Nemared root stock the tree is of medium size and medium vigor, typical of standard commercial peach varieties grown in California. Trees typically produce about 76.9 cm long lateral shoots when grown under normal commercial culture. Trees are semi-upright in habit and vase-formed in shape. The foliage is of medium density. The trees are hardy, productive, and are regular bearers.

The trunk is of medium shape and its surface texture is smooth to medium. The trunk coloration is R.H.S. 201 D (gray) at a height of 30 cm above the ground, and R.H.S. 200 D (brown) at a height of 60 cm above ground. The circumference of the trunk is approximately 70 cm at a height of 30 cm above the ground for an eight year-old tree. The branches are medium to slender in shape and have a surface texture that is smooth to medium, as well. The branches are semi-glossy to dull in surface appearance and Brown 200C in color. Lenticels are medium to few and medium to large in size, averaging 1.44 per square centimeter and are 5.9 mm long average.

LEAVES

In general, leaves are medium in size, having an average length of about 19.5 cm and an average width of about 3.2 cm. Leaves are lanceolate in outline and upfolded in profile. Leave blade tips curve downwardly at an acute angle. The leaf margin is serrate, and the undulation of the margin is medium. The leaf is acuminate at the apex, U-shaped at the base, and of medium thickness. The upper surface of the leaf is about Yellow-Green 147A in color, and of weak glossiness. The upper leaf surface is rugose with a semi-glossy to dull appearance; pubescence is absent. The lower leaf surface is about Yellow-Green 147B in color, and weak in glossiness. Pubescence is absent from the lower surface which has a rugose texture and a dull appearance.

The petiole is medium to short in length and it has a thickness that is medium to thick. There is an average of 3.7 globose glands (about Yellow-Green 153D in color) alternately positioned on both the leaf base and the petiole. Stipules fall off.

Wood (leaf) buds are small to medium in size and ovoid in shape. Their position, relative to the shoot, is adpressed. Their support in small and decurrent. The time of bud burst is medium.

On flowering shoots anthocyanin coloration is present in medium intensity. The shoots are of thin to medium thickness, about 0.4 cm. Intermode length is medium, about 2.2 cm. Buds are generally isolated on one-year-old shoots and the ratio of wood (leaf) buds to flowering shoots is about 9:11.

FLOWERS

Flower buds are hardy, of medium size and length, plump, and freely positioned. Buds are pubescent and about Greyed-Orange 165A in color.

Flowers attain full bloom by about March 3 in Wasco, Kern County, Calif. — a time of bloom that is medium as compared with similar varieties in the growning area. Blooms have a medium duration and the diameter of the fully opened flower is about 4.2 cm. The shape of the bloom is rosaceous and its petals are free to slightly overlapping. The fully opened flower is about Red-Purple 62D in color. The peduncle is short in length and medium in thickness. The pubescence of the peduncle is of medium density to fully pubescent. Flowers are self-fertile.

The receptacle is of medium depth. Pubescence is present on both the inner surface (at white bud stage) and the outer surface. The pubescence of the inner surface is of medium density to fully pubescent; whereas, the outer surface is fully pubescent.

Sepals are adpressed to petals, broad ovate in shape, and have no pubescence on the inner surface. Pubescence is present on the outer surface and is of medium density to fully pubescent. None of the flowers have exhibited double sepals.

Petals are medium in size, about 1.5 cm wide and 2.0 cm long, circular in shape, have short claw length, medium margin waviness, and a wide base angle. The division of the upper margins is slightly notched, and pubescence is absent on both inner and outer surfaces. The inner and outer surfaces are about Red-Purple 62D in color. No flowers having double petals have been observed.

The stigma is level with the anthers. The anthers are about Red-Purple 61B in color just before dehiscence. Pollen is about Yellow 13A in color. Stamens are perigynously positioned. The number of pistils is sometimes more than one but the frequency of supplementary pistils is few. The ovary and style are both pubescent. The ovary displays a medium density of hairs and the style displays a medium to slight density of hairs.

FRUIT

The fruit, as described, was ripe at maturity on May 14, 1993. The fruit at firm ripe maturity is medium in size and has an axial diameter of 5.8 cm and a transverse diameter in the suture plane of 6.1 cm. At right angles to the suture plane, the diameter is about 6.2 cm, thus indicating a slight unsymmetrical to globose shape. The position of the maximum diameter is towards the stem end of the fruit. The fruit is symmetric about the suture line and ripens early. Fruits are approximately 103 to 149 grams.

The fruit is for market use and has a good keeping quality and good shipping quality. The tree and fruit exhibit good resistance to insects and diseases, and exhibit no unusual susceptibilities when grown under commercial conditions.

The suture extends from the base to the apex but is discontinuous and has a slight-marked depression beyond the pistil point. The ventral surface is rounded slightly, and the lips are equal. The apex is slighty depressed and is medium to sparsely pubescent. The pistil base is persisting.

The stem cavity is flaring and elongated in the suture plane with the suture showing on both sides. The depth of the cavity is about 0.9 cm, and its breadth is about 2.9 cm. The base of the fruit is rounded. The apex is short is shape and the pistil point is apical in shape.

The stem is about 0.9 cm in length and is of medium size and glabrous; adherence to the stone is medium to weak. The skin is of medium texture, tenacious to the flesh, and has medium to thin in thickness. The skin is without roughness or reticulation and shows no tendency to crack in dry season. Ground color of the skin is about Red-Purple 13B and the over color of the skin is about Red-Purple 60B. Down is scant, short, and does not roll up when rubbed. Bloom is absent.

The color of the flesh, including at the surface of the pit cavity, is about Yellow-Orange 14C. Amygdalin is wanting and juice is moderate. The flesh has a medium sugar content. The flesh texture is melting and the fruit has tender to medium fibers. Fruit ripens evenly, has a distinct aroma, is subacid, and is of good eating quality. The stone (endocarp) is about 7.6 grams.

The stone is semi-free and retains short fiber-like threads along the ridges. The stone is medium in size, being about 3.3 cm in length, 2.5 cm in breadth, 1.9 cm thick, and has a stalk end width of about 0.6 cm. The angle of the stalk end is obtuse. The form of the stone in profile is elliptical and cuneate toward the apex. The form in ventral view is globular to sub-globular. The stone's base is oblique, its apex pointed, and its hilum is narrow to oval in shape. The position of the stone's maximum breadth is toward the middle and the sides are generally equal. The surface of the stone is irregularly furrowed near the base and is pitted throughout. An outgrowing keel; is absent. The ridges are rounded and continuous; the pits are circular and elongated. The ventrical edge of the stone is medium to thick without a wing toward the base and the dorsal edge is narrowly grooved throughout. The color of the stone when dry is about Greyed-Yellow 162B. The stone has a slight tendency to split in a dry season.

What is claimed is:

1. A new variety of peach tree cv. Supechnine, as illustrated and described herein.

* * * * *